(12) United States Patent
Remon et al.

(10) Patent No.: US 8,231,375 B2
(45) Date of Patent: Jul. 31, 2012

(54) PROCESS AND APPARATUS FOR CONTINUOUS WET GRANULATION OF POWDER MATERIAL

(75) Inventors: Jean-Paul Remon, Melle (BE); Chris Vervaet, Kachtem (BE); Eseldin Keleb, Gent (BE); An Vermeire, Nevele (BE)

(73) Assignee: Universiteit Gent, Ghent (BE)

( * ) Notice: Subject to any disclaimer, the term of this patent is extended or adjusted under 35 U.S.C. 154(b) by 32 days.

(21) Appl. No.: 13/009,309

(22) Filed: Jan. 19, 2011

(65) Prior Publication Data

US 2011/0108646 A1 May 12, 2011

Related U.S. Application Data

(62) Division of application No. 10/536,520, filed as application No. PCT/EP03/13327 on Nov. 26, 2003, now Pat. No. 7,910,030.

(60) Provisional application No. 60/429,214, filed on Nov. 26, 2002.

(51) Int. Cl.
 *B29B 7/42* (2006.01)
 *B29B 7/46* (2006.01)
 *B29B 9/08* (2006.01)
(52) U.S. Cl. .............................. 425/202; 366/79; 366/83
(58) Field of Classification Search .................. None
See application file for complete search history.

(56) References Cited

U.S. PATENT DOCUMENTS

| 3,642,406 A | 2/1972 | Irving |
| 3,730,663 A | 5/1973 | Hare |
| 3,749,375 A * | 7/1973 | Hermann et al. ............... 366/82 |
| 4,416,606 A | 11/1983 | Sugano et al. |

(Continued)

FOREIGN PATENT DOCUMENTS

WO  WO 01/89679  11/2001

OTHER PUBLICATIONS

Amidon et al., "A Theoretical Basis for a Biopharmaceutic Drug Classification: The Correlation of in Vitro Drug Product Dissolution and in Vivo Bioavailability," *Pharm. Res.*, 12:413-420 (1995).

(Continued)

*Primary Examiner* — Mary F Theisen
(74) *Attorney, Agent, or Firm* — Clark & Elbing LLP

(57) ABSTRACT

An apparatus for wet granulating a powder material comprises:—a barrel having a granulation chamber and being provided with a first inlet (1) for receiving said powder material and for supplying it to said granulation chamber and with a second inlet (2) for receiving a granulating liquid and for supplying it to said granulation chamber, said granulation having an aperture (9) for discharge of granules from said barrel, and—a transporting means (S) for advancing said powder material toward the end of said granulation chamber while granulating it with the aid of said granulating liquid, said transporting means (S) comprising a first transport zone (4) at its rear end, an agglomeration zone (5) downstream from the first transport zone (4) and a second transport zone (8) at its front end, said first inlet (1) and said second inlet (2) being positioned above the first transport zone (4), wherein said aperture (9) has a shape tightly fitting the terminal portion of the transporting means (S) for directly discharging said granules from the granulation chamber. The apparatus is useful for continuously wet granulating biologically-active ingredient formulations, chemicals, detergents and foodstuffs.

15 Claims, 2 Drawing Sheets

U.S. PATENT DOCUMENTS

| | | | |
|---|---|---|---|
| 4,607,797 | A | 8/1986 | Enikolopow et al. |
| 4,890,996 | A | 1/1990 | Shimizu |
| 5,018,671 | A | 5/1991 | Tanimoto et al. |
| 5,240,400 | A | 8/1993 | Fujimoto et al. |
| 5,382,377 | A | 1/1995 | Raehse et al. |
| 6,174,851 | B1 | 1/2001 | Harth et al. |
| 6,499,984 | B1 | 12/2002 | Ghebre-Sellassie et al. |
| 2006/0006258 | A1 | 1/2006 | Remon et al. |

OTHER PUBLICATIONS

Aulton, "Pharmaceutical Granulation Equipment," Found in: *Pharmaceutics: The Science of Dosage Form Design*, Publisher Churchill Livingstone, 1$^{st}$ Edition, pp. 623-625 (1989).

Gamlen et al., "Continuous Extrusion Using a Baker Perkins MP50 (Multipurpose) Extruder," *Drug Dev. and Ind. Pharm.*, 12:1701-1713 (1986).

International Preliminary Report on Patentability for International Patent Application PCT/EP03/13327, dated Apr. 7, 2005.

International Search Report for International Patent Application PCT/EP03/13327, mailed Apr. 23, 2004.

Keleb et al., "Continuous Twin Screw Extrusion for the Wet Granulation of Lactose," *Int. J. Pharm.*, 239:69-80 (2002).

Leuenberger, "New Trends in the Production of Pharmaceutical Granules: Batch Versus Continuous Processing," *Eur. J. Pharm. Biopharm.* 52:289-296 (2001).

Lindberg, "Continuous Wet Granulation," *Manufacturing Chemist*, pp. 35-38 (1988).

Martin, "In the Mix: Continuous Compounding Using Twin-Screw Extruders," www.devicelink.com retrieved Jun. 20, 2001.

Office Action for U.S. Appl. No. 10/536,520, dated Nov. 17, 2008.

Office Action for U.S. Appl. No. 10/536,520, dated Sep. 18, 2009.

Office Action for U.S. Appl. No. 10/536,520, dated Apr. 1, 2010.

Notice of Allowance for U. U.S. Appl. No. 10/536,520, dated Oct. 19, 2010.

Official Communication for European Patent Application No. 03 780 069.5, dated May 23, 2007.

Official Communication for European Patent Application No. 03 780 069.5, mailed Jun. 26, 2009.

Rauwendaal, *Polymer Extrusion*, 3$^{rd}$ ed. New York: Hanser Publishers, 460-497 (1994).

* cited by examiner

PROCESS AND APPARATUS FOR CONTINUOUS WET GRANULATION OF POWDER MATERIAL

CROSS-REFERENCE TO RELATED APPLICATIONS

This application is a divisional of U.S. patent application Ser. No. 10/536,520, filed Jul. 25, 2005, which is the U.S. National Stage of international application PCT/EP2003/013327, filed Nov. 26, 2003, which, in turn, which claims the benefit of the filing date of U.S. Provisional patent application 60/429,214, filed Nov. 26, 2002.

This invention relates to the field of particle design technology. In particular, it relates to a process and an apparatus for the continuous wet granulation of powder materials, which provide an improved granulation yield and a better controlled quality of the granules obtained. This invention is therefore of specific interest for a wide range of industries including mineral processing, agricultural products, detergents, pharmaceuticals, food stuffs, fertilisers and chemicals. In the pharmaceutical area, it is more particularly useful for making tablets, effervescent granules and for filling hard capsules or sachets.

BACKGROUND OF THE INVENTION

Powders intended for compression into tablets for the pharmaceutical and healthcare industries must possess two essential properties: fluidity and compressibility. Fluidity is required so that the material can be transported through the hopper of a tabletting machine and so that adequate filling of the dies occurs in the tabletting machine to produce tablets of a consistent weight. Although powder flow can be improved mechanically by the use of vibrators, the latter can cause powder segregation and stratification. Powder flow properties can also be increased by incorporating minute amounts of a glidant such as fumed silicium dioxide or by granulation. Compressibility is the property of forming a stable, intact compact mass when pressure is applied. Some materials are known to compact better than others, e.g. paracetamol is poorly compressible whereas lactose compresses well, however as a general rule granulation improves compressibility. The same concerns apply to detergent powders intended for making high-density detergent granules and for compression into detergent pressings.

In applications of granules other than tablets, compressibility is usually not a concern, however granulation yield, granule strength and homogeneity of particle size distribution remain the basic requirements of industries involved in such applications and uses.

Granulation is a process of particle size enlargement of powdered ingredients which is carried out to confer fluidity, and optionally compressibility, to powder systems. Ideally, granulation should be relatively dust free (reduced dustiness minimises losses, inhalation and explosion risks during further use of the granules, such as tabletting) and provide an as small percentage of both fine and coarse particles as possible, and granules should be robust enough to withstand handling without breaking down. Other desired properties of granulated products include improved flow and handling which facilitates controlled metering; increased bulk density; reduced pressure loss for fluid flow through a packed bed; controlled dissolution rates; and substantially maintained surface area of the original particles.

Granulation is a particle design technology which finds application in a wide range of industries including mineral processing, agricultural products, detergents, pharmaceuticals, foodstuffs, bed packings for blast furnaces, catalysts, fertilisers and chemicals. Improper granulation causes significant problems in down-stream industrial processes such as caking, segregation and poor tabletting performance.

A wet method for the preparation of tablets for the pharmaceutical industry is the wet granulation process which involves a number of stages as follows. First, the drug substance is blended, if needed, with an inert diluent or filler (such as lactose or dicalcium phosphate) in a powder mixer in order to produce a uniform dispersion of the drug in the filler. Then in a second step the blended mixture is wetted by means of a liquid phase or solvent including, if needed, a binder (also known as adhesive or granulating agent or binding agent). The liquid phase or solvent must be volatile, so that it can be easily removed by drying, and non-toxic. It may be for instance water or a lower alcohol, such as isopropanol, ethanol or methanol, either alone or in combination. Because of their flammability and the consequent requirement for flame-proof equipment, organic solvents are used only for water-sensitive drugs or effervescent drug formulations or when a rapid drying time is required. Suitable binders include polyvinylpyrrolidone, acacia mucilage, gelatin, cellulose derivatives and starch mucilage. The binder is usually introduced at this stage as a solution or dispersion in the liquid phase, or the binder may also be mixed in the dry powder (the so-called "dry binder addition"). The wetting step is usually carried out in the same apparatus as the blending step. The damp mass obtained is then passed through a coarse sieve, usually of mesh size 1-2 mm, yielding particles, for instance by means of an oscillating granulator in which a rotor oscillating about its horizontal axis passes the damp material through the screen, or by means of a comminutor containing a number of rapidly revolving blades. After the granulation step, granules are now dried by means of a tray drier or a fluidised bed drier or by vacuum or microwave, resulting in a coarse free-flowing solid. The granule size at this point being usually considerably larger than required for tabletting (the usual average granule size for tabletting being in a range from about 250 to 700 μm), a sizing step including a comminution stage followed by sieving will usually be needed for breaking agglomerates of granules and removing the fine material which can be recycled. After the sizing step, granules are ready for blending, if needed, with additives such as lubricants, glidants, disintegrants, flavours, colorants and the like, before being transported to the compressing device where they are compressed in a die by the application of forces via two punches.

Extrusion is another way of producing a relatively dense granule, such as may be suitable for tabletting, from a low density material. An extruder typically comprises a barrel having a chamber; means for supplying material to be mixed and extruded to said chamber, a shaft in said chamber with material advancing means thereon such as an extrusion screw for advancing material toward one end of said chamber, and a die assembly mounted on the front end of said shaft and having extrusion die port means, such as one or more profiled or slot-shaped orifices, through which said material has to be forced to produce an extrudate of the required section, so that a specific pressure gradient is created within the die. For instance, U.S. Pat. No. 3,642,406 discloses a mixer-extruder combination of the latter type, further having means for revolving and reciprocating the shaft to mix and advance the material, wherein the die assembly has radially extending extrusion die port means and includes a rearwardly extending sleeve spaced radially from the shaft to define material issuing passage means leading to said port means. U.S. Pat. No.

5,240,400 discloses another embodiment of a screw-type extrusion granulating apparatus for extruding a moistened powder material into granules, said apparatus comprising a die in the shape of a dome and having a plurality of extrusion openings oriented radially with respect to the dome shape of said die and selected to be of a size corresponding to the desired diameter of the granules, i.e. even as small as about 0.3 to 0.6 mm. FIG. 2 of this patent clearly illustrates the maximum pressure reached in the area of the extrusion die. U.S. Pat. No. 4,890,996 also discloses a continuous granulator of the double-screw type for continuously melting, kneading and granulating macromolecular or resin materials, the said granulator including a mechanism by which the degree of kneading can be controlled and prevents lateral communication between the screw ends, the said granulating machine including a cutting unit having a screen and dies.

Although continuous processing would offer significant advantages (automation; reduction of batch to batch variation, labour cost and processing time) over batch production of pharmaceutical compositions, granulation techniques until now have been mainly confined to the use of mixer granulators and fluidised bed granulators. Although continuous granulating machines are widely used in the resin and polymer industry, very rare use has been made of continuous extrusion for granulating drug formulations prior to tabletting in the pharmaceutical or veterinary industry or for granulating food components or food additives. A short review of such few attempts is now provided herewith. Gamlen et al. in *Drug Development and Industrial Pharmacy* (1986) 12:1701-1713 disclosed production of paracetamol extrudates with a high drug loading (80% by weight) in the presence of 20-28% water by means of a Baker-Perkins MP50 mixer/extruder, explaining that the latter offers significant advantages by reducing the number of pieces of equipment required for extrudate manufacture. The extrudates thus obtained within a temperature range from 31 to 50° C. however had a high incidence of defects such as surface roughness and shark skinning (i.e. cracks penetrating deeply into the core of the extrudate). Furthermore, in the absence of a binder (hydroxypropylmethylcellulose), extrusion was associated with partial screen blockage at all moisture contents and marked irregularities in the rate of extrusion. Increasing the moisture content up to 28% resulted in an improvement in extrudate quality but also in more extensive clumping together of the extrudates to form aggregates. Summarising, Gamlen et al. faced the problems of equipment blocking at the lower water contents and of particle sticking at the higher water contents which still remain to be solved. In addition, the relatively high water contents used by Gamlen et al. necessarily induce a long post-processing drying step which is therefore significantly power-consuming and economically inefficient.

Similarly, Lindberg in *Manufacturing Chemist* (December 1988) 35-38 reported the continuous wet granulation of an effervescent mixture of 2 parts anhydrous citric acid and 1 part sodium bicarbonate by means of dehydrated ethanol as the granulating liquid in an extruder Baker Perkins MPF 50D comprising a feeding zone, a mixing zone and a discharge zone, wherein the powder inlet port is located above the feeding zone of the extruder and the granulating liquid inlet port is located above the mixing zone, wherein the paddles in the mixing zone provide intense shear mixing and wherein the discharge screws in the discharge zone help in developing the die pressure in the die plate which is attached at the extruder exit. While using residence time from 17 to 45 seconds, but without specifying ethanol concentration, Lindberg reported first the obtention of extrudates consisting of 5-10 mm long wet spaghetti, then after 30 minutes operation appearance suddenly changed to about 10 cm long spaghetti, indicating a blockage of the liquid injection nozzle. Summarising, Lindberg experienced the same technological problems as Gamlen et al. (cited supra), confirming significant shortcomings of the extrusion granulation technique in the drug formulation industry, and indicating the desirability for improvements in the granulating equipment for that purpose.

Leuenberger in *European Journal of Pharmaceutics and Biopharmaceutics* (2001) 52:289-296 reports on a quasi-continuous production line developed by Glatt A G (Pratteln, Switzerland) for avoiding scale-up problems in the pharmaceutical industry, the said production line being based on the principle of a semi-continuous production of mini-batches (sub-units) in a high-shear mixer/granulator which is connected to a continuous multicell-fluidised bed dryer. The article additionally reports on using this production line for granulating mixtures of lactose and maize starch with the aid of about 14.3% to 18.6% by weight of purified as the granulating liquid, again inducing a time- and power-consuming drying step. While admitting that this concept is not entirely continuous, the article insists on the fact that a technology transfer from processes with high production volumes has so far been less than successful in the case of continuous processing of pharmaceutical granules, and that in the pharmaceutical industry the batch-type wet granulation process cannot be so easily transformed into a continuous process.

Keleb et al. in *International Journal of Pharmaceutics* (2002) 239:69-80 disclosed a continuous twin screw extrusion process for the wet granulation of α-lactose monohydrate and investigated the influence of various parameters on the properties of granules and of tablets obtained by compressing the granules after wet sizing the extrudates, oven-drying and sieving. The process involved a co-rotating twin screw extruder having a feeding zone, a first mixing zone, a first transport zone, a second mixing zone, a second transport zone, and a die zone feeding to a die block mounted on the extruder barrel. While, like previously cited authors, indicating that precautions should be taken to avoid machine blocking, Keleb et al. reported a granulation yield of 60% and a tensile strength of 0.50 MPa for the resulting compacted tablets. Again these results show that there is still room for significant improvement before achieving an efficient and reproducible continuous process applicable to the pharmaceutical industry.

Similar observations can be derived from prior art in the detergent industry. For instance, U.S. Pat. No. 5,018,671 provides an apparatus for the continuous granulation of high-density detergent granules of a predetermined size from a detergent powder, comprising a granulation chamber, a feeding port located at the top of the granulation chamber, a first discharging port located at the bottom of the granulation chamber, a second discharging port located at the side wall of the granulation chamber, one or more horizontally rotating stirring blades attached to a rotational shaft positioned at the bottom of the granulation chamber for stirring and mixing the detergent powder, and one or more vertically rotating grinding blades located above the one or more stirring blades and attached to a rotational shaft positioned at the side wall of the granulation chamber for grinding and classifying coarse detergent particles. The same reference provides a process for operating the said apparatus, comprising the steps of continuously feeding a detergent powder into the granulation chamber, granulating the detergent powder by stirring and mixing the powder with the one or more horizontally rotating stirring blade, and continuously discharging the high-density detergent granules thus formed through the second discharging port. Operating the apparatus at a material temperature of 25°

C. to 45° C. with an average retention time of 5 to 10 minutes achieved detergent granules with a bulk density of up to 0.7 g/cm$^3$.

U.S. Pat. No. 5,382,377 discloses producing detergent pressings by a process comprising extruding a homogeneous premix containing a plasticizer or lubricant into strands through a perforated die under a pressure of 25 to 200 bar, forming compacted granules thereof, and pressing said compacted granules under a pressure of 1 to 300 bar. This process achieves high-performance detergents with densities up to 1.5 g/cm$^3$.

Both International patent application published as WO 01/89679 and U.S. Pat. No. 6,499,984 disclose a single pass continuous processing system for producing pharmaceutical granulation, comprising:
(a) powder and liquid feeders to feed at least one pharmaceutically active ingredient and additives;
(b) a twin screw wet granulator-chopper device for granulating the active ingredient and additives received from the powder and liquid feeders into a wet granular product said twin screw wet granulator-chopper including a housing surrounding said device, said housing including a non-extruding opening at the outlet thereof;
(c) conveying, loading, and levelling means for conveying the wet granulation from the outlet of said twin screw wet granulator-chopper, loading the wet granulation on a dryer belt, and levelling the wet granulation to a desired height;
(d) a drying apparatus for receiving the wet granulation from the dryer belt and drying the wet granulation using dielectric energy;
(e) conveying means for transporting the dried granulation from the drying apparatus for size reduction;
(f) a mill for reducing the dried granulation to particles of a desired size; and
(g) control means for controlling process variables of at least one of the powder and liquid feeders, the twin screw wet granulator-chopper, the conveying, loading, and levelling means, the drying apparatus, the conveying means, and the mill to optimize production of pharmaceutical granulation.

This continuous processing system appears as a combination of known equipment, since for instance twin-screw granulators are well known from U.S. Pat. Nos. 4,890,996 and 3,730,663, and choppers (i.e. devices for cutting into small pieces) are common in pharmaceutical granulation equipment, as disclosed by Aulton in *Pharmaceutics, the Science of Dosage Form Design* (1988) 623-625.

Thus, there is a strong consensus in the prior art that continuous granulation equipment is based either on high-shear mixers or fluid bed granulators or on extruding means including a die and/or developing a pressure at the extruder exit. At the same time, there is a strong need in the art for improving the long-term operating conditions of a wet granulation process, in particular for drug formulations and pharmaceutical compositions, by solving the recurrent problems of machine blocking reported by the various authors herein-above. It has been postulated that these problems may be due to the use of granulating equipment originally designed for resins and polymers whereas pharmaceutical compositions and foodstuffs, contrary to resins and polymers, are susceptible of physical and/or chemical interaction with the granulating liquid (usually water and/or a lower alcohol). There is also a need in the art for improving the granulation yield of a wet granulation process during long-term operations, i.e. for high production volumes. There is also a need in the art for the design of granulation equipment suitable for various powder materials, including chemicals, catalysts, detergents, drug formulations and foodstuffs, and which is simple and inexpensive in construction and maintenance. Furthermore, there is a need in the art for making drug formulations which have a reduced occurrence of certain defects such as shark skinning. Finally, there is a need in the art for making granules from pharmaceutical compositions or excipients which, when compacted into tablets, provide improved tablet properties, in particular higher tensile strength. Desirably, the continuous granulation process and equipment should be suitable for a very wide range of biologically-active substances, including those which are moisture-sensitive and/or heat-sensitive, i.e. should be able to operate at short residence times and low temperatures. Also desirably, it should be able to save energy and reduce the overall processing time by shortening the subsequent drying step duration. All the above cited needs constitute the various problems which the present invention intends to solve.

SUMMARY OF THE INVENTION

The present invention is based on departing from the well-established consensus in the art that an extrusion die and the consequent application of a forcing pressure is needed for the wet granulation of certain powder materials, in particular those which are susceptible of physical and/or chemical interaction with the granulating liquid (usually water and/or a lower alcohol). The present invention also departs from the teaching of WO 01/89679 by not requiring the combination of successive means (c) to (g) or the presence of a chopper in the device (b) of the disclosed system, i.e. by significantly simplifying the continuous processing equipment of this prior art.

The invention is also based on the unexpected finding that a solution to the various above cited problems can be obtained in a simple and inexpensive manner by the proper design of a wet granulation equipment, in particular by avoiding the use of a die, die block, die plate or die screen, or any other similar device having the function or result of forcing the granulate to produce an extrudate of a required section by creating a specific pressure gradient in the terminal portion of said equipment. Correspondingly, this invention provides an improved and more efficient continuous wet granulation process and apparatus involving, e.g. consisting of, a transporting means such a single or double screw, wherein the granulate material produced in the last section of the transporting means is directly discharged without being submitted to any pressure gradient such as the one caused by a die, die block, die plate, die screen or similar pressure-inducing means. Incidentally, the invention is also based on the unexpected finding that the various above cited problems can be overcome while minimising the amount of the granulating liquid being used and consequently minimising the duration and power consumption of the granule drying step. The invention additionally provides granules of all kinds, in particular foodstuff granules, mineral ore granules, agricultural product (e.g. fertiliser) granules, detergent granules, catalyst granules, chemical granules, as well as biologically active ingredient (e.g. pharmaceutical) granules, all the aforesaid granules being obtainable by means of the above-mentioned novel continuous wet granulation process or by continuously operating the said wet granulation apparatus. In the pharmaceutical area, said granules are suitable for various applications including but not limited to making tablets with improved properties or effervescent granules or for filling hard capsules (e.g. based on gelatine or hydroxypropylmethylcellulose) or sachets.

DETAILED DESCRIPTION OF THE INVENTION

Figure 1:
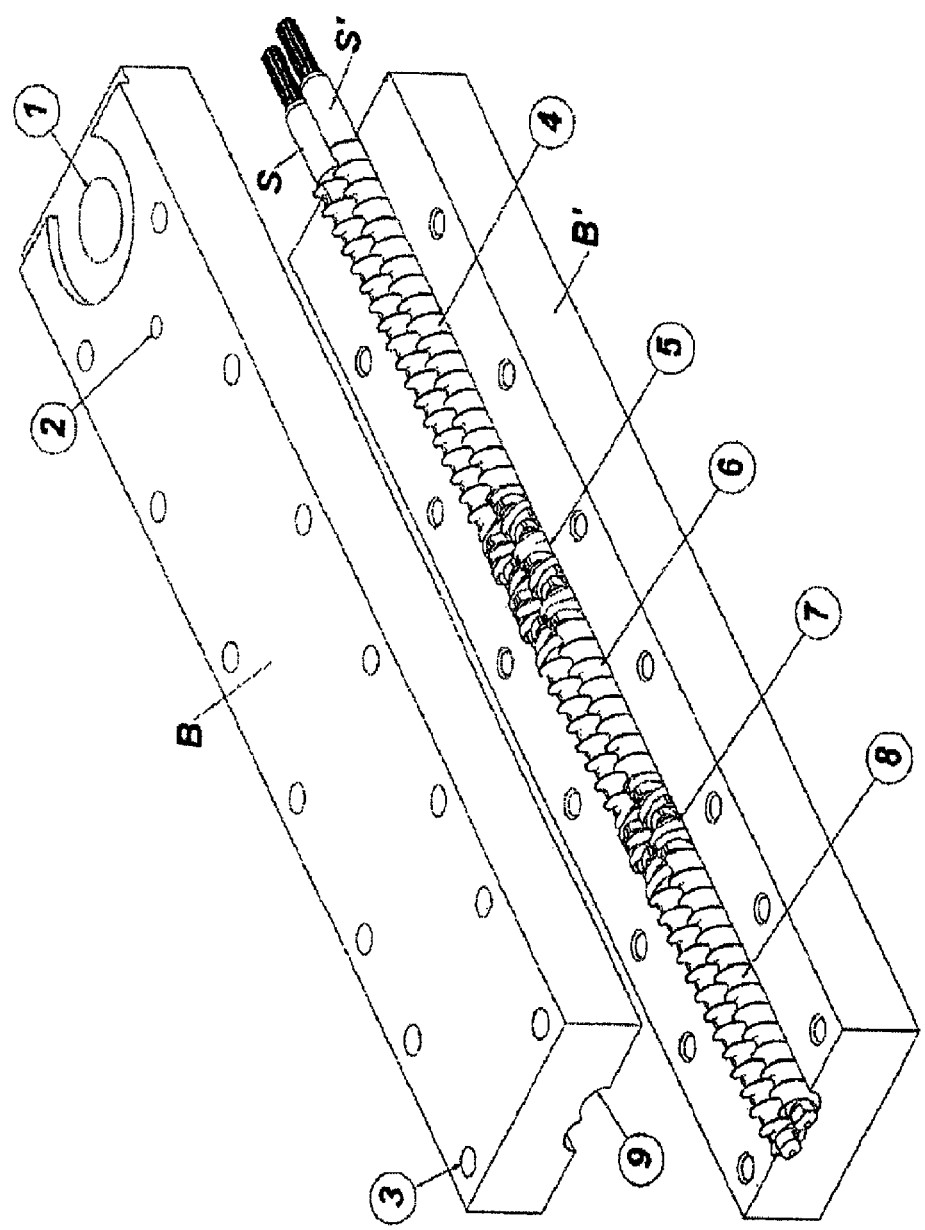
FIG. 1 shows a view in perspective of a preferred embodiment of a continuous wet granulation apparatus according to the present invention.

The present invention will be described with reference to certain embodiments and drawings but the present invention is not limited thereto but only by the attached claims. The embodiments are given by way of example only.

A first object of the present invention is an apparatus for the continuous wet granulation of a powder material. This apparatus, which is now described by reference to FIG. 1, comprises or consists of:

- a barrel having a granulation chamber provided between a first part (B) and a second part (B') of said barrel, the first part (B) being provided with at least one first inlet (1) connected with said granulation chamber for receiving said powder material and for supplying it to said granulation chamber and with at least one second inlet (2) connected with said granulation chamber for receiving a granulating liquid and for supplying it to said granulation chamber, said granulation chamber having an aperture (9) for discharge of granules from said barrel, and
- at least one continuously operated transporting means (S) provided in said granulation chamber for advancing said powder material toward the end of said granulation chamber while granulating said powder material with the aid of said granulating liquid, each said transporting means (S) comprising at least one first transport zone (4) at its rear end, an agglomeration zone (5) downstream from the first transport zone (4), and a second transport zone (8) at its front end, said at least one first inlet (1) and said at least one second inlet (2) of the barrel being positioned above the at least one first transport zone (4) of each said at least one transporting means (S), wherein said aperture (9) has a shape tightly fitting the terminal portion of said at least one transporting means (S) for directly discharging said granules from the granulation chamber without developing a pressure gradient at the exit of the granulation chamber. The second transport zone is a granule forming zone.

Without wishing to be bound by theory, the following functions of the apparatus of the invention are assumed. First, the powder material and the granulating liquid are mixed while being transported in the first transport zone (4), thus resulting in a wet powder material. Secondly, the wet powder material is agglomerated, e.g. densified or compacted into an agglomerated material or compact mass in the agglomeration zone (5). Last, the agglomerated material or compact mass breaks up into granules in the second transport zone (8). Thus it should be understood that, even though the agglomeration zone (5) contributes to advancing the powder material through the transporting means (S), i.e. achieves some transport, the agglomeration zone (5) substantially distinguishes over the transport zones (4, 8) by effecting most if not all of the particle size enlargement of the powder material. By contrast, the second transport zone (8) contributes to breaking-up the densified compact mass produced upstream thereof. Contrary to the extrusion equipment of the prior art, the granulation chamber aperture (9) and the terminal portion of the transporting means are shaped similarly so that no pressure gradient can result from their respective arrangement at the exit of the granulation chamber.

In a particular embodiment of the invention, each said at least one transporting means (S) further comprises one or more additional transport zones (FIG. 1 shows two such additional transport zones 6 and 8) and one or more additional agglomeration zones (7), each agglomeration zone (5, 7) being positioned between two transport zones (4, 6, 8). Again without wishing to be bound by theory, it is assumed that for the suitable wet granulation of some powder materials one single agglomeration zone (5) may not be sufficient, whatever its length or the amount of granulating liquid, to achieve the desired granule properties (e.g. size distribution). In such a case, a suitable efficiency of the apparatus of the invention may however be obtained by merely repeating the sequence of an agglomeration zone followed by a transport zone until the target size distribution is achieved. The total number of transport zones and agglomeration zones of the apparatus according to the invention is not a critical parameter and may be adapted to the specific powder material to be granulated, depending on the desired granule properties (such as particle size distribution and/or friability) and the desired production rate, by routine optimisation experiments well within the knowledge of the skilled person. It is however important, whatever that number, that the first zone (4) at the rear end (i.e. the upstream zone close to the powder material feeding inlet) and the last zone (8) at the front end (i.e. the downstream zone close to the terminal portion of the transporting means S) of the transporting means (S) are both transport zones between which are arranged one or more agglomeration zones. Thus more preferably the number of transport zones exceeds by one the number of agglomeration zones. The respective lengths of the transport zones and agglomeration zones of the transporting means in the apparatus according to the invention are not a critical parameter either and may be routinely adapted to the specific needs by using standard knowledge in the art and/or a reasonable number of iterative experiments, depending upon the specific powder material to be granulated, the desired granule properties (such as particle size distribution and/or friability) and the desired production rate. For general guidance, it is however preferred that the cumulative lengths of the agglomeration zone(s) represent from about 8% to about 30%, more preferably from about 10% to about 25%, of the length of the transporting means (S). The geometrical configuration of the agglomeration zone(s) is not a critical parameter of the invention. For instance, the agglomeration zone may comprise a number of mixing paddles, the positioning (i.e. the angle) and the thickness of which may be varied within wide ranges, as is already familiar to the skilled person.

In another particular embodiment of the invention, said transporting means is a rotating transporting means such as a single screw or a multiple screw, preferably a twin screw.

In another particular embodiment of the invention, the length to diameter ratio of each screw is preferably within a range from about 15 to about 60, more preferably within a range from about 20 to about 30. In yet another particular embodiment of the invention, the length of each transporting means is preferably within a range from about 25 cm to about 4 m, more preferably from about 50 cm to about 2 m, depending upon the amount of powder material to be transported per unit of time and, in the case of a rotating transporting means, upon the rotation speed and the screw diameter.

In yet another particular embodiment of the invention, the respective dimensions (e.g. the diameter in case of circular openings as shown in FIG. 1) of the first inlet (1) for receiving the powder material and of the second inlet (2) for receiving the granulation liquid are such that the weight ratio of the granulating liquid to the powder material may be preferably not above 16:100, more preferably not above 12:100, most preferably not above 8:100, and/or such that the weight ratio of the granulating liquid to the powder material may be preferably not below 2:100, preferably not below 4:100, without causing a risk of blocking of the apparatus of the invention in continuous operation.

A second object of the present invention is a process for the continuous wet granulation of a powder material which may be operated or carried out in the apparatus described hereinbefore. Such a process comprises, or consists of, the steps of:
(a) feeding a powder material to a first transport zone of a transporting means,
(b) feeding a granulating liquid to said first transport zone of said transporting means,
(c) transporting said powder material and said granulating liquid from said first transport zone to an agglomeration zone of said transporting means downstream of said first transport zone for agglomerating said wet powder material,
(d) transporting said agglomerated material from said agglomeration zone to a second transport zone of said transporting means downstream of said agglomeration zone for producing granules, and
(e) directly discharging said granules from said second transport zone of said transporting means without submitting said granules to any pressure gradient.

The discharging may be described as a free flow discharge.

Thus the process according to the invention may be carried out by operating an apparatus of the type shown in FIG. 1. In a particular embodiment of the invention, the continuous wet granulation process may further comprise the step of transporting said agglomerated material from said agglomeration zone to said second transport zone of said transporting means through one or more combinations of an additional intermediate transport zone followed by an additional intermediate agglomeration zone. As previously indicated, it is preferred for overall efficiency that the total number of transport zones (transporting or breaking up steps) exceeds by one the total number of agglomeration zones (agglomeration steps). In a particular embodiment of the invention, the transporting steps (c) and (d) are carried out by a rotating transporting means such as a single screw or a multiple screw, preferably a twin screw. In a particular embodiment, the process of the invention further comprises a granule drying step (f) subsequent to step (e). This drying step may be performed in any conventional drying equipment but, especially when applied to pharmaceutical granules, is preferably and advantageously shorter than required in the extrusion processes of Gamlen and Lindberg cited above, because of the lower amount of the granulating liquid being used in this invention.

In a particular embodiment of the invention, the residence (retention) time of said powder material in said transporting means is preferably in the range of about 5 seconds to about 180 seconds, more preferably from about 10 seconds to 180 seconds and most preferably from about 20 seconds to about 60 seconds, depending upon parameters such as the specific powder material, the advancement speed of the transporting means (e.g. the rotation speed of the rotating transporting means) and the transporting means configuration (e.g. its length). Residence times higher than 180 seconds may also be admissible in particular circumstances.

In a particular embodiment of the invention, the granulating liquid is a substance or mixture of substances which preferably does not chemically interfere with or alter the powder material to be granulated. Therefore the granulating liquid will be selected according to the characteristics, such as moisture sensitivity, of the specific powder material concerned. For economic and safety reasons, water is usually preferred as the granulating liquid, but lower alcohols such as methanol, ethanol or isopropanol, or mixtures thereof with water in various proportions, may constitute suitable alternatives when moisture sensitivity is a limitation inherent to the powder material. For energetic considerations, the amount of the granulating liquid used should be as low as possible. It is an unexpected advantage of this invention over the extrusion processes of the prior art that the amount of the granulating liquid (in particular water) may be reduced to a range preferably from about 2% by weight to about 12% by weight, more preferably from about 4% by weight to about 8% by weight, of the powder material without adversely affecting the overall efficiency of the process. However higher amounts of the granulating liquid, e.g. up to about 16% by weight, with respect to the powder material may also be used under certain circumstances without a disadvantage other than increasing the subsequent drying time or the amount of energy required in a subsequent granule drying step.

In another particular embodiment, the continuous process of the invention may be carried out at a temperature within a range from about 10° C. to about 50° C., in particular from about 10° C. to about 25° C. or from about 25° C. to about 40° C., e.g. by regularly or continuously controlling the temperature barrel and if necessary by cooling the said barrel in order to substantially maintain its temperature within the specified range, although incidental short temperature increase up to 45° C. will in most cases not affect the granule quality or output. In yet another particular embodiment, the process of the invention includes a granule drying step (f), subsequent to the discharging step (e), which may be performed in any conventional drying equipment, such as oven, radio-frequency generating apparatus and the like, with the purpose of substantially eliminating the granulation liquid which may still be present after step (e). If desired for certain applications, the dried granules may further be subjected to one or more subsequent dry sieving steps, with the purpose of further refining their particle size range, and to one or more subsequent dry milling steps with the purpose of recovering a significant portion of the bigger particles.

An unexpected advantage of the process of this invention is a higher total granulation yield than is achieved by the granulation techniques of the prior art such as high shear granulation or extrusion granulation. Using the above-mentioned preferred conditions, the process of the invention is able, if desired, to produce granules wherein the fraction of particles having a size above about 1,400 μm is negligible. After drying, the granules produced may be dry sieved e.g. through a 1,000 μm sieve and the fraction above 1,000 μm may quite easily be dry milled (e.g. by means of an oscillating granulator) in order to recover an additional fraction of granules under 1,000 μm and to mix it with the main fraction of granules under 1,000 μm which directly resulted from dry sieving the granules produced in the wet granulation process of the invention. The total granulation yield Y is thus defined as the sum of the yield Y1 in a certain desirable granule fraction (e.g. the granule fraction between 250 and 1,000 μm, as shown in the following examples) directly resulting from the wet granulation process of the invention and of the yield Y2 in the same desirable granule fraction resulting from conventional dry milling of the granules from the wet granulation process having a particle size greater than the upper size (e.g. 1,000 μm in this example) of said desirable granule fraction. It should be understood that the above particle size limit values (250 and 1,000 μm) are given for illustration purpose only and that other limit values could be used alternatively without altering the essential teachings of the invention. The total granulation yield that can be achieved by the process and apparatus of the invention is highly dependent upon the relevant powder material. With respect to most pharmaceutically active ingredients, it is in excess of about 40% even for poorly flowable, poorly compactable or poorly water-soluble materials like paracetamol. In most cases, i.e. for foodstuffs or drugs having standard flowability, total granulation yields that can be achieved are preferably above 60%, more preferably in excess of 70%, most preferably in excess of 75% and may even reach as high as about 90%. Yet another unexpected advantage of this invention is the high level of reproducibility (i.e. the low standard deviation) of the granule properties (such as particle size distribution and friability) obtained by performing the said process. This reproducibility in turn significantly participates in the quality, namely uniformity of distribution of a biologically active ingredient, of products that may be obtained from such granules such as, but not limited to, by compacting or compressing them into tablets or incorporating them into capsules.

Another advantage of this invention is that it allows to granulate materials that are difficult to granulate with other available techniques, i.e. it can be used for a broader range of materials than the conventional high shear and fluid bed granulation techniques.

A third object of the present invention is a granule population obtainable by, preferably obtained by, performing the process or operating the apparatus as described herein-above. Such process and apparatus can result in a granule population having a size, preferably an average size, within a range preferably from about 250 µm to about 1,000 µm, more preferably from about 250 µm to about 700 µm, which is entirely suitable for most conventional industrial applications, in particular pharmaceutical and cosmetic applications such as effervescent granules, filling hard capsules (e.g. based on gelatine or hydroxypropyl-methylcellulose) or sachets, or for making tablets by compression in a conventional compacting machine.

A fourth object of the present invention is a finished product such as solid shaped article (in particular a tablet) obtainable, preferably a tablet obtained, from a granule population obtained by performing the process, or by operating the apparatus, of this invention. The said finished product may be of any solid shape, such as a tablet, a composite article (e.g. including an inner core and an outer layer), a capsule and the like, and may be obtained from the said granule population by any known processing technique, such as but not to limited to compression (tablets) or filling (capsules). Thanks to the inherent advantageous properties (in particular size homogeneity) of the granule population of the invention, the resulting finished product, e.g. tablet, may have better properties than a tablet made from granules obtained by the high shear granulation process or the extrusion granulation technique or the granulator-chopper apparatus of the prior art.

The chemical constitution, particle size or other physical property of the powder material that may be used in the continuous wet granulation process of this invention are not critical parameters. The powder material may be selected for instance from foodstuffs, mineral ores, agricultural products (e.g. fertilisers), detergents, catalysts, chemicals, as well as biologically active ingredients and compositions containing the latter together with suitable conventional additives, modifiers or excipients.

Suitable examples of foodstuffs include animal foodstuff such as vitamins, proteins, lipids, sugars, cellulose for poultry, fish, pigs, dogs, cats, and cattle in general, as well as human foodstuff such as flower, sugar, instant preparations for soup or puddings.

Suitable examples of catalysts include any type of zeolites or catalysts, including for instance catalysts suitable for packing fluidised bed reactors.

Suitable examples of detergents include those containing typical ingredients of detergents, for example water-soluble emulsifiers and synthetic surface-active agents including anionic and non-ionic surfactants (such as also defined below with regard to pharmaceutically acceptable excipients), builders, inorganic electrolytes, re-deposition inhibitors, foam inhibitors, bleaches and bleach activators, optical brighteners, enzymes, fabric softeners and dyes and fragrances. Suitable organic and inorganic builders for detergents are soluble and/or insoluble components which show a mildly acidic, neutral or alkaline reaction and which are capable of precipitating or complexing calcium ions. Suitable and, in particular, ecologically safe builders are e.g. finely crystalline, synthetic water-containing zeolites of the NaA type in detergent quality. Their particle size is normally in the range from 1 to 10 µm. Their content is generally from 0 to 40% by weight, of the detergent composition, based on anhydrous substance. Other builders which may be used in particular together with said zeolites include (co)polymeric polycarboxylates, such as polyacrylates, polymethacrylates and, in particular, copolymers of acrylic acid with about 50% to 10% maleic acid and an average molecular weight from about 50,000 to 100,000. Suitable, but less preferred compounds of this class are copolymers of at least about 50% acrylic or methacrylic acid with vinyl ethers, such as vinyl methyl ether. Other organic builders are e.g. non-polymeric polycarboxylic acids preferably used in the form of their sodium salts, such as citric acid or nitrilotriacetic acid. Suitable inorganic electrolytes are the bicarbonates, carbonates, borates or silicates of the alkali metals also known as "washing alkalis". Suitable re-deposition inhibitors for detergent compositions, being able to keep the soil separated from the fibers suspended in the wash liquor, are water-soluble, generally organic colloids such as e.g. the water-soluble salts of polymeric carboxylic acids, glue, gelatine, salts of ether-carboxylic acids or ether-sulfonic acids or acidic sulfuric acid esters of cellulose or starch. Water-soluble polyamides containing acidic groups, soluble starch preparations (e.g. degraded starch or aldehyde starches), polyvinylpyrrolidone, carboxymethyl cellulose (sodium salt), methyl cellulose, methyl hydroxyethylcellulose and mixtures thereof are also suitable. Foam inhibitors include soaps, preferably natural and synthetic soaps having a high content of C18-C24 fatty acids, organopolysiloxanes, paraffins, waxes, microcrystalline waxes and mixtures thereof with silanized silica. Suitable bleaches include sodium perborate tetra- or monohydrate, peroxycarbonates, peroxypyrophosphates, citrate perhydrates and peracidic salts or peracids, such as perbenzoates, peroxophthalates, diperazelaic acid or diperdodecanedioic acid. Suitable bleach activators include N-acyl and O-acyl compounds such as N,N'-tetraacylated diamines, and carboxylic anhydrides and esters of polyols such as glucose pentaacetate. Suitable optical brighteners include derivatives or alkali metal salts of diaminostilbene disulfonic acid such as 4,4'-bis-(2-anilino-4-morpholino-1,3,5-trazin-6-ylamino)-stilbene-2,2-disulfonic acid or similar compounds which, instead of the morpholino group, contain a diethanolamino group, a methylamino group, an anilino group or a 2-methoxyethylamino group. Suitable enzymes may be selected from proteases, lipases, amylases and mixtures thereof, e.g. as obtained from bacterial strains or fungi such as *Bacillus subtilis, Bacillus licheniformis* and *Streptomyces griseus*, and may be adsorbed onto carriers and/or encapsulated into shell-forming substances in order to protect them against premature decomposition.

The term "biologically active ingredient" as used herein refers to therapeutic, diagnostic, cosmetic and prophylactic agents as well as other agents, e.g. selected from insecticides, pesticides, herbicides, plant growth regulators, fertilisers, crop treatment agents, anti-microbial agents (in particular fungicides and bactericides), admissible for use in plants, animals and humans. Thus the biologically active granules made according to this invention may be for pharmaceutical use, cosmetic use, veterinary use or for plant treatment. The therapeutic agent can be selected for its specific properties such as for instance its anti-thrombotic, anti-inflammatory, anti-proliferative or anti-microbial efficiency. The latter include for instance anti-microbial agents such as broad spectrum antibiotics for combating clinical and sub-clinical infection, for example gentamycin, vancomycine and the like. Other suitable therapeutic agents are naturally occurring or synthetic organic or inorganic compounds well known in the art, including non-steroidal anti-inflammatory drugs, proteins and peptides (produced either by isolation from natural sources or recombinantly), hormones (for example androgenic, estrogenic and progestational hormones such as oestradiol), bone repair promoters, carbohydrates, antineoplastic agents, antiangiogenic agents, vasoactive agents, anticoagulants, immunomodulators, cytotoxic agents, antiviral agents, antibodies, neurotransmitters, oligonucleotides, lipids, plasmids, DNA and the like. Suitable therapeutically active proteins include e.g. fibroblast growth factors, epidermal growth factors, platelet-derived growth factors, macrophage-derived growth factors such as granulocyte macrophage colony stimulating factors, ciliary neurotrophic factors, tissue plasminogen activator, B cell stimulating factors, cartilage induction factor, differentiating factors, growth hormone releasing factors, human growth hormone, hepatocyte growth factors, immunoglobulins, insulin-like growth factors, interleukins, cytokines, interferons, tumor necrosis factors, nerve growth factors, endothelial growth factors, osteogenic factor extract, T cell growth factors, tumor growth inhibitors, enzymes and the like, as well as fragments thereof. Suitable diagnostic agents include conventional imaging agents (for instance as used in tomography, fluoroscopy, magnetic resonance imaging and the like) such as transition metal chelates. Suitable anti-microbial agents include e.g. halogenated phenols, chlorinated diphenylethers, aldehydes, alcohols such as phenoxyethanol, carboxylic acids and their derivatives, organometallic compounds such as tributyltin compounds, iodine compounds, mono- and polyamines, sulfonium and phosphonium compounds; mercapto compounds as well as their alkaline, alkaline-earth and heavy metal salts; ureas such as trihalocarbanilide, isothia- and benzisothiazolone derivatives. Suitable insecticides include natural ones, e.g. nicotine, rotenone, pyrethrum and the like, and synthetic ones like chlorinated hydrocarbons, organophosphorus compounds, biological insecticides (e.g. products derived from *Bacillus thuringiensis*), synthetic pyrethroids, organosilicon compounds, nitro-imines and nitromethylenes. Suitable fungicides include e.g. dithiocarbamates, nitrophenol derivatives, heterocyclic compounds (including thiophtalimides, imidazoles, triazines, thiadiazoles, triazoles and the like), acylalanines, phenylbenzamides and tin compounds. Suitable herbicides include e.g. trichloroacetic and aromatic carboxylic acids and their salts, substituted ureas and triazines, diphenyl ether derivatives, anilides, uraciles, nitriles and the like. Suitable fertilizers include e.g. ammonium sulphate, ammonium nitrate, ammonium phosphate and the like, and mixtures thereof.

Therapeutically active agents which are advantageously incorporated into the granules of the present invention preferably belong to all permeability and solubility classes of the Biopharmaceutical Classification System according to G. Amidon et al. in *Pharm. Res.* (1995) 12:413-420, in particular the two classes of poorly soluble drugs, i.e. Class II and Class IV of the said classification. As will be appreciated by those skilled in the art, these drugs belong to various therapeutic classes including, but are not limited to, beta-blockers, calcium antagonists, ACE inhibitors, sympathomimetic agents, hypoglycaemic agents, contraceptives, α-blockers, diuretics, anti-hypertensive agents, anti-psoriatics, bronchodilators, cortisones, anti-mycotics, salicylates, cytostatics, antibiotics, virustatics, antihistamines, UV-absorbers, chemotherapeutics, antiseptics, estrogens, scar treatment agents, antifungals, antibacterials, antifolate agents, cardiovascular agents, nutritional agents, antispasmodics, analgesics, antipyretics, anti-inflammatory agents, coronary vasodilators, peripheral vasodilators, antitussive, muscle relaxants, tranquilisers, antiarrythmic agents, anticoagulants, antiemetics, expectorants, antidiabetic agents and the like.

This invention is suitable e.g. for wet granulating formulations of the following therapeutically active ingredients or cosmetic agents: acebutolol, acetohexamide, acetylcysteine, acetylsalicylic acid, acyclovir, ajamaline, alendronate, alfuzosine, alprazolam, alfacalcidol, allantoin, allopurinol, alverine, ambroxol, amikacin, amlodipine, amiloride, aminoacetic acid, amiodarone, amitriptyline, amlodipine, amoxicillin, ampicillin, amylobarbitone, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefatroxil, cefazolin, cefixime, cefotaxime, ceftazidime, ceftriaxone, cefuroxime, cephalosporins, cetirizine, chloramphenicol, chlordiazepoxide, chlorhexidine, chlorpheniramine, chlortalidone, choline, cyclosporin, cilastatin, cimetidine, ciprofloxacin, cisapride, cisplatin, citalopram, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavine mononucleotide, fluconazole, flunarizine, fluorouracil, fluoxetine, flurbiprofen, furosemide, gallopamil, gemfibrozil, Ginkgo bitoba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocamitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, paroxetine, penicillins, phenobarbital, pentoxifylline, phenoxymethylpenicillin, phenylephrine, phenylpropanolamine, phenytoin, physostigmine, piroxicam, polymyxin B, povidone iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, risperidone, rutoside, saccharin, salbutamol, salcatonin, salicylic acid, simvastatin, somatotropin, sotalol, spironolactone, sucralfate, sulbactam, sulfamethoxazole, sulfasalazine, sulpiride, tamoxifen, tegafur, teprenone, terazosin, terbutaline, terfenadine, tetracaine, tetracycline, theophylline, thiamine, ticlopidine, timolol, tranexamic acid, tretinoin, triamcinolone acetonide, triamterene, triazolam, trimethoprim, troxerutin, uracil, valproic acid, verapamil, folinic acid, zidovudine, zopiclone, enantiomers thereof, organic and inorganic addition salts (including acid salts and base salts) thereof, solvates (such as hydrates and alcoholates) thereof and mixtures thereof, in particular mixtures in synergistic proportions.

Other biologically active ingredients for the purpose of the invention are vitamins, include those of the A group, of the B group (which means, besides B1, B2, B6 and B12, also compounds with vitamin B properties such as adenine, choline, pantothenic acid, biotin, adenylic acid, folic acid, orotic acid, pangamic acid, carnitine, p-aminobenzoic acid, myo-inositol and lipoic acid), vitamin C, vitamins of the D group, E group, F group, H group, I and J groups, K group and P group.

This invention is also suitable for therapeutically active ingredients (drugs) having a water-solubility below about 2.5 mg/ml, even between 0.1 and 1 mg/ml (i.e. "very slightly soluble" as defined in the United States Pharmacopeia), even below 0.1 mg/ml (i.e. "practically insoluble" as defined in the United States Pharmacopeia), even below about 5 µg/ml and may even have a water-solubility as low as about 0.2 µg/ml, at room temperature and physiological pH. Non-limiting examples of such drugs include for instance hydrochlorothiazide, nimodipine, flufenamic acid, mefenamic acid, bendroflumethiazide, benzthiazide, ethacrinic acid, nitrendipine and diaminopyrimidines, including enantiomers thereof, organic and inorganic addition salts (including acid salts and base salts) thereof, and solvates (such as hydrates and alcoholates) thereof. Suitable examples of such poorly soluble diaminopyrimidines include, without limitation, 2,4-diamino-5-(3,4,5-trimethoxybenzyl)pyrimidine (trimethoprim), 2,4-diamino-5-(3,4-dimethoxy-benzyl)pyrimidine (diaveridine), 2,4-diamino-5-(3,4,6-trimethoxybenzyl)pyrimidine, 2,4-diamino-5-(2-methyl-4,5-dimethoxybenzyl)pyrimidine (ormetoprim), 2,4-diamino-5-(3,4-dimethoxy-5-bromobenzyl)pyrimidine, 2,4-diamino-5-(4-chloro-phenyl)-6-ethylpyrimidine (pyrimethamine), and analogues thereof.

This invention is suitable for wet granulating formulations of said biologically active ingredients (e.g. drugs) which further comprise one or more physiologically (e.g. pharmaceutically) acceptable excipients, such as emulsifiers or surface-active agents, thickening agents, gelling agents or other additives, and wherein the active ingredient (e.g. drug) loading, i.e. the proportion or content of the active ingredient (e.g. drug) in the formulation, may vary through wide ranges. For instance said active ingredient content may be at least about 0.1% by weight, preferably at least 1% by weight, more preferably at least 5% by weight. Furthermore, said active ingredient content may be at most about 99% by weight, preferably at most 95% by weight, more preferably at most 50% by weight.

Emulsifiers or surface-active agents suitable for therapeutically active formulations or detergent compositions include water-soluble natural soaps and water-soluble synthetic surface-active agents. Suitable soaps include alkaline or alkaline-earth metal salts, unsubstituted or substituted ammonium salts of higher, preferably saturated, fatty acids ($C_{10}$-$C_{22}$), e.g. the sodium or potassium salts of oleic or stearic acid, or of natural fatty acid mixtures obtainable form coconut oil, palm oil or tallow oil. Synthetic surface-active agents (surfactants) include anionic, cationic and non-ionic surfactants, e.g. sodium or calcium salts of polyacrylic acid; sulphonated benzimidazole derivatives preferably containing 8 to 22 carbon atoms; alkylarylsulphonates; and fatty sulphonates or sulphates, usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide) and the like.

Suitable emulsifiers further include partial esters of fatty acids (e.g. lauric, palmitic, stearic or oleic) or hexitol anhydrides (e.g., hexitans and hexides) derived from sorbitol, such as commercially available polysorbates. Other emulsifiers which may be used include, but are not limited to, adducts of polyoxyethylene chains (1 to 40 moles ethylene oxide) with non-esterified hydroxyl groups of the above partial esters, such as the surfactant commercially available under the trade name Tween 60 from ICI Americas Inc.; and the poly(oxyethylene)/poly(oxypropylene) materials marketed by BASF under the trade name Pluronic.

Suitable structure-forming, thickening or gel-forming agents for the biologically active formulation granules of the invention include highly dispersed silicic acid, such as the product commercially available under the trade name Aerosil; bentonites; tetraalkyl ammonium salts of montmorillonites (e.g. products commercially available under the trade name Bentone) wherein each of the alkyl groups may contain from 1 to 20 carbon atoms; cetostearyl alcohol and modified castor oil products (e.g. a product commercially available under the trade name Antisettle).

Gelling agents which may be included into the biologically active ingredient granules of the present invention include, but are not limited to, cellulose derivatives such as carboxymethylcellulose, cellulose acetate and the like; natural gums such as arabic gum, xanthum gum, tragacanth gum, guar gum and the like; gelatin; silicium dioxide; synthetic polymers such as carbomers, and mixtures thereof. Gelatin and modified celluloses represent a preferred class of gelling agents.

Hydrophilic cellulose derivatives may be used as well as pharmaceutically acceptable excipients for granulating formulations of therapeutically active ingredients according to the invention. The term "hydrophilic" herein refers to a cellulose derivative or polymer having groups, preferably non-ionizable groups, that are capable of hydrogen bonding, in particular of association with water molecules at physiologically relevant pH. Suitable examples of hydrophilic cellulose polymers that can be used in the present invention include polymers having ether-linked substituents, for instance hydroxy-alkylalkylcelluloses (wherein the alkyl group preferably has from 1 to 4 carbon atoms) such as hydroxypropylmethylcellulose. Hydroxypropylmethylcellulose is cellulose 2-hydroxypropyl methyl ether (hereinafter referred to as HPMC). It is a non-ionic water-soluble ether of methylcellulose which is insoluble in hot water but dissolves slowly in cold water. Being used extensively as a drug tablet excipient, HPMC is commercially available under various trade names. Suitable grades of HPMC include a low viscosity grade such as Methocel K100 from Dow Chemical, a high viscosity grade such as Methocel K100M, and other types such as the Metolose 90SH series from Shinetsu.

Amphiphilic materials may be used as well as pharmaceutically acceptable excipients for granulating formulations of therapeutically active ingredients according to the invention. The term "amphiphilic" herein refers to a material having both a hydrophobic portion, for instance comprising aliphatic or aromatic hydrocarbon groups, and a hydrophilic portion. Suitable examples of such amphiphilic materials include those having both a portion derived from a glyceride and a portion derived from a polyethylene glycol ester. For instance, it is suitable to use polyglycosylated glycerides as an amphiphilic material excipient in the present invention. The expression "polyglycosylated glycerides" as used herein denotes a mixture of mono-, di- and triglycerides with polyethylene glycol (PEG) mono- and diesters of $C_8$-$C_{15}$ fatty acids with a molecular weight preferably between about 200 and about 600, optionally further including glycerol and/or free PEG, the hydrophilic-lipophilic balance (HLB) value of which is controlled by the chain length of the PEG and the melting point of which is controlled by the chain length of the fatty acids, of the PEG and of the degrees of saturation of the fatty chains, and thus of the starting oil. Similarly the expression "$C_8$-$C_{18}$ fatty acids" as used herein denotes mixtures in various proportions of caprylic acid, capric acid, lauric acid, myristic acid, palmitic acid and stearic acid, when these acids are saturated, and the corresponding unsaturated acids. As is well known to the skilled person, the proportions of these fatty acids may vary as a function of the starting oils. Examples of the latter include, but are not limited to, saturated polyglycolized $C_8$-$C_{10}$ glycerides, such as the PEG-8 caprylate-caprate glyceride esters sold by Gattefosse Corporation under the tradename Labrasol; PEG-6 caprylic/capric glycerides sold by Huls Aktiengesellschaft under the trade name Softigen 767; PEG-60 corn glycerides sold by Croda under the trade name Crovol M-70; Ceteareth-20 sold by Henkel Corporation under the trade name Eumulgin B2; diethyleneglycol monoethyl-ethers sold by Gattefosse Corporation under the trade name Transcutol; a mixture of $C_8$-$C_{18}$ saturated polyglycosylated glycerides having a melting point within a range of about 42-48° C. and a HLB within a range of about 8 to 16 such as sold by Gattefosse Corporation under the trade names Gelucire 48/09, Gelucire 44/14 and Gelucire 42/12; and mixtures thereof in various proportions.

Other optional excipients which may be present in the biologically active formulation granules made according to the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetra-acetic acid; flavoring agents such as natural vanillin; buffers such as citric acid or acetic acid; extenders or bulking agents such as silicates, diatomaceous earth, magnesium oxide or aluminum oxide; densification agents such as magnesium salts; and mixtures thereof.

When the biologically active formulation is intended for making effervescent granules, it should necessarily include sodium bicarbonate and one or more weak acids, such as citric acid or tartaric acid, acting as a carbon dioxide liberator. Such effervescent granules can be made for the purpose of effervescent tablets, e.g. for cleaning artificial teeth.

The selection of the optimal excipients and their proportion in the biologically active formulation granules of the present invention depends, in a manner which is well known to the skilled person, on a series of parameters such as, but not limited to, the specific biologically-active ingredient to be formulated, the end-user requirements for the granules, the load (i.e. weight proportion) of the biologically-active ingredient in the granules and the required biologically-active ingredient (e.g. drug) release characteristics (in particular kinetics).

The continuous wet granulation process and apparatus according to the invention provide, inter alia, the following advantages:

- technical and economical improvement in the long-term operating conditions of wet granulation, in particular for drug formulations, pharmaceutical compositions and foodstuffs, by avoiding machine blocking, reducing power consumption, avoiding excessive temperatures which could be detrimental to the powder material, and increasing the total granulation yield, while eliminating the wet sizing step required in a continuous extrusion process,
- design of a granulation equipment suitable for various powder materials, including those which are difficult to granulate with other available techniques, such as detergents, drug formulations of all kinds and foodstuffs, which equipment is simple and inexpensive in construction and maintenance,
- a technology which is fully compatible with the Good Manufacturing Principles of the pharmaceutical industry,
- making drug formulations which have a reduced occurrence of certain defects such as shark skinning, and
- making granules from pharmaceutical compositions or excipients which, when compacted into tablets, provide improved tablet properties, in particular improved tensile strength.

In view of the above technical and economical advantages, the present invention is useful and extremely valuable to the pharmaceutical industry, the chemical, detergent and mining industries, and the foodstuff industry.

The following examples are provided for illustrative purpose only, and should in no way be interpreted as limiting the scope of the present invention.

EXAMPLE 1

Twin Screw Wet Granulating Apparatus

Figure 2:
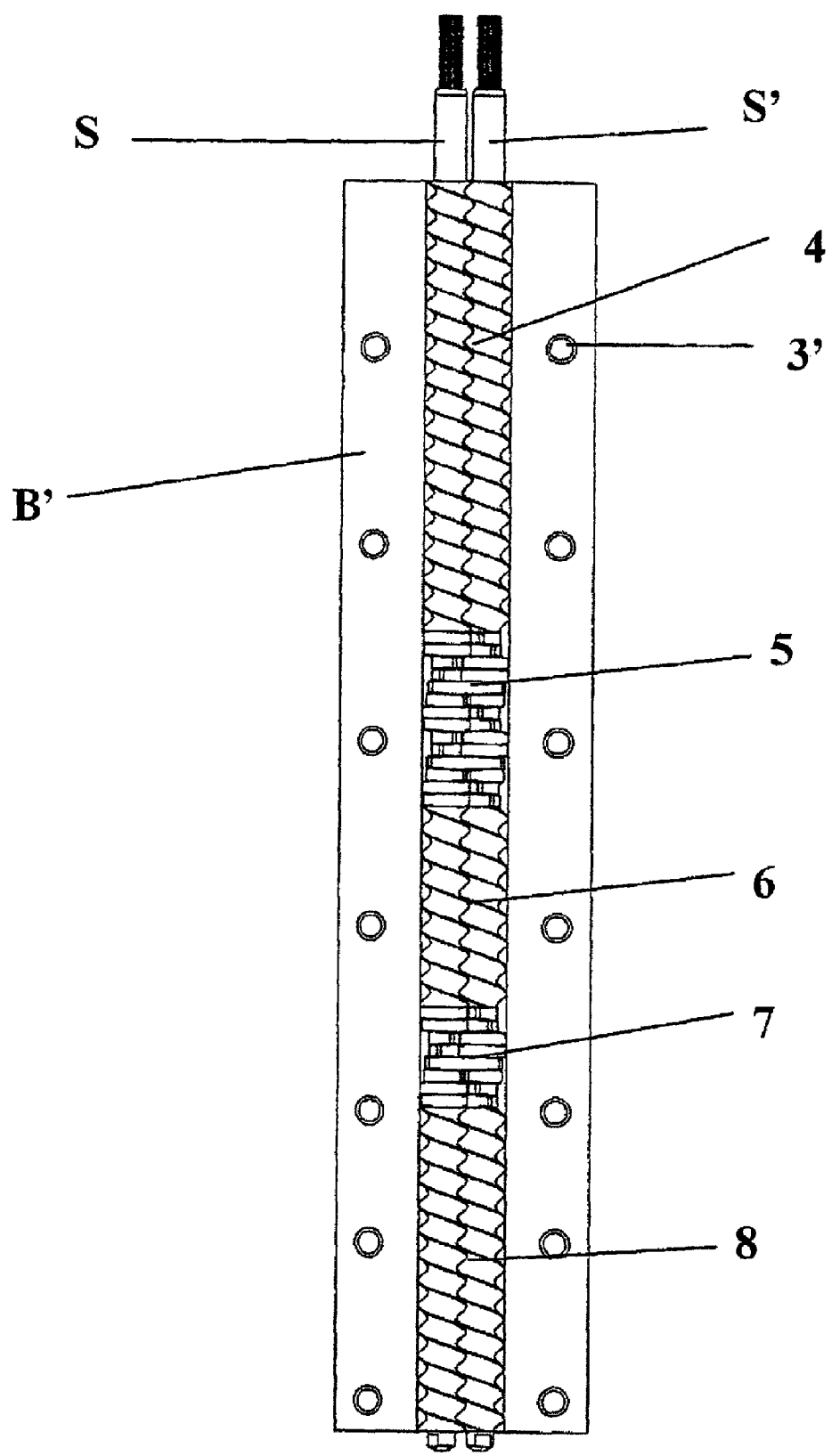
FIG. 2 shows a partial top view of a preferred embodiment of a continuous wet granulation apparatus according to the present invention, including a twin screw and the lower part of a barrel.

A preferred embodiment of an apparatus according the invention for the wet granulation of a powder material is shown in the attached FIGS. 1 and 2. Said apparatus comprises a barrel having a housing defining a granulation chamber for receiving the powder material and a granulating liquid.

The said granulation chamber is thus provided between a first upper part (B) and a second lower part (B') of said barrel. The granulation chamber is opened towards the outside of said barrel through an aperture (9). The first upper part (B) of the barrel is provided with a first inlet (1) connected with said granulation chamber for receiving said powder material and for supplying it to said granulation chamber. The first upper part (B) of the barrel is provided with a second inlet (2) connected with said granulation chamber for receiving a granulating liquid and for supplying it to said granulation chamber. The first upper part (B) of the barrel is further provided with a series of holes (3) for receiving screws (not shown on the figures) for attaching said first upper part (B) to the second lower part (B') via a series of corresponding holes (3') in said second lower part (B'). Clearly, any similar fixing means could be used for said attachment.

The apparatus further comprises two rotatably driven screws (S, S') each provided in said granulation chamber for advancing said powder material toward the end of said granulation chamber while granulating said powder material with the aid of said granulating liquid. The motor driving the two screws (S, S') is not shown on the figure. Each of the two screws (S, S') has a total length of 47.5 cm and a diameter of 1.9 cm and comprises, in the direction of advancement of the powder material:

- a first transport zone (4) at its rear end, having a length of 20.9 cm,
- a first agglomeration zone (5) comprising mixing paddles and having a length of 4.75 cm,
- an intermediate transport zone (6) having a length of 6.65 cm,
- a second agglomeration zone (7) comprising mixing paddles and having a length of 2.85 cm, and
- a second transport zone (8) having a length of 12.35 cm at the front end.

As shown on the figure, the first inlet (1) and one second inlet (2) of the barrel are positioned above the first transport zone (4) of the screws (S, S').

The aperture (9) of the granulation chamber has a shape which tightly fits the terminal portions of the screws (S, S') so as to directly discharge the granulated material from the granulation chamber without passing it through an restricted section (such as the die, die block and/or die screen of the prior art) for submitting it to a pressure gradient.

EXAMPLES 2 AND 3

Twin Screw Wet Granulation of α-Lactose Monohydrate

The twin screw apparatus described in example 1 was used for the granulation of α-lactose monohydrate (commercially available from DMV, Veghel, The Netherlands) which was supplied to the first inlet (1) via a conventional feed hopper. During granulation the powder volume in the feed hopper was maintained at a constant level (85-100% of the total feeder capacity). Powder and granulation liquid feed rates were determined prior to each experiment by repeatedly weighing the powder and the liquid amount delivered over a period of 5 minutes. The granulation liquid—pure water (example 2) and/or an aqueous polyvinylpyrrolidone (hereinafter referred as PVP) solution commercially available from B.A.S.F (Ludwigshafen, Germany) under the trade name Kollidon® K30 (example 3)—was pumped into the first transport zone (4) by means of a peristaltic pump (Watson Marlow, Cornwall, United Kingdom) via the second inlet (2).

The barrel was set at a constant temperature of 25° C. and the following parameters were selected: a screw speed of 250 rpm, a total input rate of 5.6 kg.h$^{-1}$ and a water concentration (weight/weight) of 8.5% (example 2) and 7.5% (example 3) for formulations without (example 2) and with 2.5% (weight/weight) PVP (example 3), respectively. All water concentrations were based on the wet granules mass, while PVP concentration was based on dry weight.

Granules were collected 10 minutes after the process was started in order to allow the system to equilibrate. The granules were oven-dried at 25° C. for 20 hours and dry sieved first through a 1400 μm sieve and secondly through a 1,000 μm sieve. The particle size distribution of the dried granule fraction below 1,400 μm ($F_{<1400\ \mu m}$) was determined using laser diffraction (Master Sizer apparatus commercially available from Malvern, United Kingdom) after suspending the particles in air. The volume diameter ($d_v$) was used to calculate the fractions $F_{<250\ \mu m}$, $F_{250-1000\ \mu m}$ and $F_{>1000\ \mu m}$. The analysis was performed at minimal air pressure (0.4 bar) in order to avoid disagglomeration and/or disintegration of the granules during the test. The yield of the granulation process (Y1) was calculated as $F_{<1400\ \mu m}(\%) \times F_{250-1000\ \mu m}(\%)/100$, where $F_{250-1000\ \mu m}$ is the granule fraction between 250 and 1000 μm. The granule fraction having a particle size above 1,000 μm ($F_{>1000\ \mu m}$) was dry milled by means of a conventional oscillating granulator and the particle size distribution of the resulting dry milled granules was determined using the same laser diffraction technology as above. The yield on dry milling (Y2) (after milling of the granule fraction >1000 μm) was calculated as $F_{<1000\ \mu m}(\%) \times F_{250-1000\ \mu m}(\%)/100$. The total granulation yield was then calculated as Y=Y1+Y2.

Table 1 below indicates the average value and standard deviation of granule friability (expressed as a percentage) and the average value of the to total granulation yield Y (expressed as a percentage), depending upon the granulating liquid used.

The granule friability was determined in a friabilator (PTFE, commercially available from Pharma Test, Hainburg, Germany), at a speed of 25 rpm for 10 minutes, by subjecting 10 g ($I_{wt}$) of the $F_{250-1000\ \mu m}$ granule fraction together with 200 glass beads (having a mean diameter of 4 mm) to falling shocks. Afterwards the glass beads were removed and the weight of the granules retained on a 250 μm sieve ($F_{wt}$) was determined after vibrating for 5 minutes (using a vibrator Retsch VE 1000, Germany) at an amplitude of 2 mm. The friability (expressed as a percentage) was calculated as:

$$f = (I_{wt} - F_{wt}/I_{wt}) \times 100.$$

EXAMPLES 4 AND 5

Tablets Obtained from α-Lactose Monohydrate Granules

Granule populations ($F_{250-710\ \mu m}$) prepared according to examples 2 and 3 were blended with 0.5% (weight/weight) magnesium stearate (<90 μm) (commercially available from BUFA, Brussels, Belgium) in a Turbula mixer (commercially available from W.A. Bachofen, Basel, Switzerland) for 1 minute. Tablets (250 mg) were prepared using an eccentric compression machine (commercially available from Korsch EKO, Berlin, Germany) equipped with a flat faced double punch of 9 mm at a compression force of 10 kN per tablet. The hardness, thickness and diameter of the tablets (n=6) were determined (according to PTB 311 Pharma Test, Hainburg, Germany) after a 24 hour storage period at 25° C. and 60% room humidity. The tablet tensile strength T (expressed in MPa) was calculated using the equation described by Fell and Newton (1968): $T=2F/\pi.d.t$ wherein F, d and t denote the diametral crushing force, the tablet diameter and the tablet thickness, respectively.

Table 1 below indicates the average value and standard deviation of the tablet tensile strength T (expressed in MPa).

TABLE 1

| EXAMPLE | Friability (%) | Yield Y (%) | Tensile strength (MPa) |
|---|---|---|---|
| 2 | 21 ± 3.5 | 80 | n.a. |
| 3 | 12 ± 2.6 | 78 | n.a. |
| 4 | n.a. | n.a. | 0.80 ± 0.08 |
| 5 | n.a. | n.a. | 1.21 ± 0.05 |

EXAMPLES 6 AND 7

Twin Screw Wet Granulation of Paracetamol

The experimental procedure of examples 2 and 3 was repeated, except that α-lactose monohydrate was replaced with paracetamol and that a water concentration (weight/weight) of 8.5% (example 6) and 7.5% (example 7) was used for formulations without (example 6) and with 2.5% (weight/weight) PVP (example 7), respectively. Table 2 below indicates the average value and is standard deviation of granule friability and the average value of the total granulation yield Y, both determined as above and expressed as percentages, depending upon the granulating liquid used.

EXAMPLE 8

Tablets Obtained from Paracetamol Granules

A granule population ($F_{250-710 \, \mu m}$) prepared according to example 7 was blended with excipients and then compressed into tablets under the same conditions as in examples 4 and 5. Table 2 below indicates the average value and standard deviation of the tablet tensile strength T (expressed in MPa).

TABLE 2

| EXAMPLE | Friability (%) | Yield Y (%) | Tensile strength (MPa) |
|---|---|---|---|
| 6 | 91 | 44 | n.a. |
| 7 | 27 | 50 | n.a. |
| 8 | n.a. | n.a. | 1.98 |

EXAMPLE 9

Twin Screw Wet Granulation of Animal Food

An animal food formulation based on sugars, proteins, lipids and starch was wet granulated with 6% by weight of water as the granulating liquid while using the process conditions of example 2. A total granulation yield of 90%, determined as in example 2, was achieved.

EXAMPLES 10 TO 12

Twin Screw Wet Granulation of Cimetidine

The experimental procedure of examples 2 and 3 was repeated, except that α-lactose monohydrate was replaced with cimetidine and that a water concentration (weight/weight) of 8.5% (example 10), 7.5% (example 11) and 15.5% (example 12) was used for formulations without PVP (example 10), with 2.5% by weight PVP (example 10) and with both 2.5% by weight PVP and 5% by weight of a crosslinked PVP, respectively. Table 3 below indicates the average value and standard deviation of granule friability and the average value of the total granulation yield Y, both determined as in example 2 above and expressed as percentages, depending upon the granulating liquid used.

EXAMPLES 13 TO 15

Tablets Obtained from Cimetidine Granules

Granule populations ($F_{250-710 \, \mu m}$) prepared according to examples 10 to 12 were blended with excipients and then compressed into tablets under the same conditions as in examples 4 and 5. Table 3 below indicates the average value and standard deviation of the tablet tensile strength T (expressed in MPa).

TABLE 3

| EXAMPLE | Friability (%) | Yield Y (%) | Tensile strength (MPa) |
|---|---|---|---|
| 10 | 27 | 60 | n.a. |
| 11 | 16 | 66 | n.a. |
| 12 | 27 | 62 | n.a. |
| 13 | n.a. | n.a. | 1.41 |
| 14 | n.a. | n.a. | 1.42 |
| 15 | n.a. | n.a. | 1.93 |

The invention claimed is:

1. An apparatus for the continuous wet granulation of a powder material, consisting essentially of:
   a barrel having a granulation chamber provided between a first part (B) and a second part (B') of said barrel, the first part (B) being provided with at least one first inlet (1) connected with said granulation chamber for receiving said powder material and for supplying it to said granulation chamber and with at least one second inlet (2) connected with said granulation chamber for receiving a granulating liquid and for supplying it to said granulation chamber, said granulation chamber having an aperture (9) for discharge of granules from said barrel, and
   at least one continuously operated transporting means (S) provided in said granulation chamber for advancing said powder material toward the end of said granulation chamber while granulating said powder material with the aid of said granulating liquid, each said transporting means (S) comprising at least a first transport zone (4) at its rear end and optionally one or more additional transport zones (6), an agglomeration zone (5) downstream from the first transport zone (4) and optionally one or more additional agglomeration zones (7), and a second transport zone (8) at its front end, each agglomeration zone (5, 7) being positioned between two transport zones (4, 6, 8), said at least one first inlet (1) and said at least one second inlet (2) of the barrel being positioned above the at least one first transport zone (4) of each said at least one transporting means (S),
   wherein said aperture (9) has a shape tightly fitting the terminal portion of said at least one transporting means (S) for directly discharging said granules from the granulation chamber without developing a pressure gradient at the exit of the granulation chamber.

2. An apparatus according to claim 1, wherein said transporting means (S) is a rotating transporting means.

3. An apparatus according to claim 1, wherein said transporting means (S) is a single screw.

4. An apparatus according to claim 1, wherein said transporting means (S) is a twin screw.

5. An apparatus according to claim 3, wherein the length-to-diameter ratio of the screw is within a range from 15 to 60.

6. An apparatus according to claim 4, wherein the length-to-diameter ratio of each screw is within a range from 15 to 60.

7. An apparatus according to claim 1, wherein the cumulative lengths of the agglomeration zones (5, 7) represent from 8% to 30% of the length of the transporting means (S).

8. An apparatus according to claim 2, wherein the cumulative lengths of the agglomeration zones (5, 7) represent from 8% to 30% of the length of the rotating transporting means (S).

9. An apparatus according to claim 1, wherein the cumulative lengths of the agglomeration zones (5, 7) represent from 10% to 25% of the length of the transporting means (S).

10. An apparatus according to claim 2, wherein the cumulative lengths of the agglomeration zones (5, 7) represent from 10% to 25% of the length of the rotating transporting means (S).

11. An apparatus according to claim 1, wherein the respective dimensions of the first inlet (1) for receiving the powder material and of the second inlet (2) for receiving the granulation liquid are such that the weight ratio of the granulating liquid to the powder material is not above 16:100.

12. An apparatus according to claim 1, wherein the respective dimensions of the first inlet (1) for receiving the powder material and of the second inlet (2) for receiving the granulation liquid are such that the weight ratio of the granulating liquid to the powder material is not above 12:100.

13. An apparatus according to claim 1, wherein the respective dimensions of the first inlet (1) for receiving the powder material and of the second inlet (2) for receiving the granulation liquid are such that the weight ratio of the granulating liquid to the powder material is not above 8:100.

14. An apparatus according to claim 1, wherein the respective dimensions of the first inlet (1) for receiving the powder material and of the second inlet (2) for receiving the granulation liquid are such that the weight ratio of the granulating liquid to the powder material is not below 2:100.

15. An apparatus according to claim 1, wherein the respective dimensions of the first inlet (1) for receiving the powder material and of the second inlet (2) for receiving the granulation liquid are such that the weight ratio of the granulating liquid to the powder material is not below 4:100.

* * * * *